United States Patent
Watanabe et al.

(10) Patent No.: US 10,379,475 B2
(45) Date of Patent: Aug. 13, 2019

(54) IMAGE FORMING APPARATUS PROJECTING INFORMATION ONTO INNER SURFACE OF OPEN COVER

(71) Applicant: CANON KABUSHIKI KAISHA, Tokyo (JP)

(72) Inventors: Kazuhiro Watanabe, Tokyo (JP); Kenta Koyama, Tokyo (JP); Hideki Takaoka, Kawasaki (JP); Masatoshi Lin, Kawasaki (JP); Wataru Kaku, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/825,609

(22) Filed: Nov. 29, 2017

(65) Prior Publication Data
US 2018/0157202 A1 Jun. 7, 2018

(30) Foreign Application Priority Data
Dec. 5, 2016 (JP) .................... 2016-236265

(51) Int. Cl.
*H04N 1/00* (2006.01)
*B41J 11/00* (2006.01)
(Continued)

(52) U.S. Cl.
CPC ..... *G03G 15/5016* (2013.01); *G01N 21/8806* (2013.01); *G03F 1/84* (2013.01);
(Continued)

(58) Field of Classification Search
CPC .. G03G 15/55; G03G 15/553; G03G 15/6502; G03G 15/5016; G03G 21/1604;
(Continued)

(56) References Cited

U.S. PATENT DOCUMENTS 6,091,915 A * 7/2000 Takagishi ........... G03G 15/5016
399/21
8,339,358 B2 * 12/2012 Kohara .............. G03G 15/5016
345/156
(Continued)

FOREIGN PATENT DOCUMENTS

JP        11-116909 A      4/1999
JP    2001247235 A  *  9/2001
(Continued)

OTHER PUBLICATIONS

U.S. Appl. No. 15/825,567, Kotaro Torikata, Dai Kanai, Teppei Nagata, Hideki Mori, Makoto Matsuo, Jun Shirayanagi, Kenta Koyama, Hideki Takaoka, Masatoshi Lin, filed Nov. 29, 2017.

(Continued)

*Primary Examiner* — Joseph S Wong
(74) *Attorney, Agent, or Firm* — Venable LLP

(57) ABSTRACT

An image forming apparatus includes a main assembly including an image forming portion configured to form an image on a sheet; a front cover mounted on a front side of the main assembly and configured to expose the image forming portion by being rotated from above toward below about a rotational axis crossing a vertical direction; a fixing portion configured to fix a position of the front cover in an open state; an exchange unit detachably mountable to the image forming portion in the open state of the front cover; and a projecting portion provided above the front cover in the vertical direction and configured to project information on exchange of the exchange unit onto an inner surface of the front cover in the open state when the exchange unit is to be exchanged.

10 Claims, 10 Drawing Sheets

(51) Int. Cl.
*G06K 15/00* (2006.01)
*G03F 1/84* (2012.01)
*G01N 21/88* (2006.01)
*G03G 15/00* (2006.01)
*G03G 21/16* (2006.01)

(52) U.S. Cl.
CPC ........... *G03G 15/55* (2013.01); *G03G 15/553* (2013.01); *G03G 15/6502* (2013.01); *G03G 21/1604* (2013.01); *G03G 21/1633* (2013.01); *B41J 11/0075* (2013.01); *G06K 15/408* (2013.01); *G06K 15/4025* (2013.01); *H04N 1/00015* (2013.01); *H04N 1/00037* (2013.01); *H04N 1/00082* (2013.01); *H04N 1/00249* (2013.01); *H04N 1/00267* (2013.01); *H04N 1/00954* (2013.01); *H04N 2201/0082* (2013.01); *H04N 2201/0098* (2013.01); *H04N 2201/3273* (2013.01)

(58) Field of Classification Search
CPC ........... G03G 21/1633; G06K 15/4025; G06K 15/408; H04N 1/00015; H04N 1/00037; H04N 1/00082; H04N 1/00267; H04N 1/00954; H04N 1/00249; H04N 2201/0082; H04N 2201/0098; H04N 2201/3273; B41J 11/0075; G01N 21/8806; G03F 1/84
See application file for complete search history.

(56) References Cited

U.S. PATENT DOCUMENTS

| | | | | |
|---|---|---|---|---|
| 9,972,231 | B1* | 5/2018 | Furutani | B41J 29/42 |
| 2007/0223012 | A1* | 9/2007 | Montierth | H04N 1/00249 |
| | | | | 358/1.1 |
| 2009/0213436 | A1* | 8/2009 | Takuwa | H04N 1/00384 |
| | | | | 358/442 |
| 2009/0316193 | A1* | 12/2009 | Kohara | G03G 15/5016 |
| | | | | 358/1.15 |
| 2017/0185878 | A1* | 6/2017 | Matsuo | G06K 15/4025 |
| 2018/0146118 | A1* | 5/2018 | Miyamoto | H04N 1/00267 |

FOREIGN PATENT DOCUMENTS

| | | | | |
|---|---|---|---|---|
| JP | 2009-169047 A | | 7/2009 | |
| JP | 2009298561 A | * | 12/2009 | |
| JP | 2010-008839 A | | 1/2010 | |
| JP | 2010-128120 A | | 6/2010 | |
| JP | 2018092045 A | * | 6/2018 | ......... G03G 21/1633 |

OTHER PUBLICATIONS

U.S. Appl. No. 15/825,632, Hideki Mori, Jun Shirayanagi, Dai Kanai, Teppei Nagata, Kotaro Torikata, Makoto Matsuo, Kenta Koyama, Hideki Takaoka, Masatoshi Lin, filed Nov. 29, 2017.

* cited by examiner (a)

(b)

IMAGE FORMING APPARATUS PROJECTING INFORMATION ONTO INNER SURFACE OF OPEN COVER

FIELD OF THE INVENTION AND RELATED ART

The present invention relates to an image forming apparatus for displaying operation guidance for notifying an operator of an operation procedure such as clearance of paper jam or exchange of consumables.

Conventionally, in the image forming apparatus, such as a copying machine, of an electrophotographic type, in some cases, there is a need for an operator to perform operations such as the clearance of paper jam (jamming), the exchange of the consumables and parts, supply of a developer, supply of sheets, and the like. For that reason, in the image forming apparatus, on a screen of an operating portion, operation guidance for notifying the operator of pieces of information on an operation procedure, a state of the image forming apparatus and matters to be attended to have been displayed.

However, in the case where the operation guidance is displayed on the screen of the operating portion, the operation procedure cannot be displayed in contrast with an operation object, so that the operator once stops the operation and has to see the screen of the operating portion.

Therefore, Japanese Laid-Open Patent Application (JP-A) 2010-128120 has proposed that operation guidance is displayed from a projector onto a screen or an inside surface of a front door of an image forming apparatus depending on an operation portion.

Further, JP-A 2010-8839 has proposed that operation guidance is displayed on a liquid crystal display portion provided on a sheet stacking surface of a manual feeding tray or that the operation guidance is projected from a projector onto the sheet stacking surface of the manual feeding tray.

However, in the above-described conventional constitutions, the operation of the operation object by the operator while making reference to the operation guidance remains still problematic.

That is, in the constitution of JP-A 2010-128120, the operation guidance is projected onto the inside surface of a door member opened and closed by being rotated about a rotational axis (vertical direction hinge) parallel to a vertical direction. For that reason, the operation guidance about an operation object provided in an apparatus main assembly so as to oppose the door member in a closed state of the door member cannot be displayed in contrast with the operation object while causing the operator to satisfactorily recognize the operation object. Further, in the constitution of JP-A 2010-8839, the operation guidance is displayed on the sheet stacking surface of the manual feeding tray, so that the operation guidance cannot be displayed while being contrasted with the operation object accommodated inside the door member so as to oppose the door member.

SUMMARY OF THE INVENTION

A principal object of the present invention is to provide an image forming apparatus capable of making reference to operation guidance in contrast with an operation object, provided in an apparatus main assembly so as to oppose a door member in a closed state of the door member, while allowing satisfactory recognition of the operation object visually.

Another object of the present invention is to provide an image forming apparatus capable of easily recognizing an exchange step when an exchange (replacement) part is exchanged.

According to an aspect of the present invention, there is provided an image forming apparatus comprising: a main assembly including an image forming portion configured to form an image on a sheet; a front cover mounted on a front side of the main assembly and configured to expose the image forming portion by being rotated from above toward below about a rotational axis crossing a vertical direction; a fixing portion configured to fix a position of the front cover in an open state; an exchange unit detachably mountable to the image forming portion in the open state of the front cover; and a projecting portion provided above the front cover in the vertical direction and configured to project information on exchange of the exchange unit onto an inner surface of the front cover in the open state when the exchange unit is to be exchanged.

Further features of the present invention will become apparent from the following description of exemplary embodiments with reference to the attached drawings.

DESCRIPTION OF EMBODIMENTS

An image forming apparatus according to the present invention will be specifically described with reference to the drawings.

Embodiment 1

1. General Structure of Image Forming Apparatus

Figure 1:
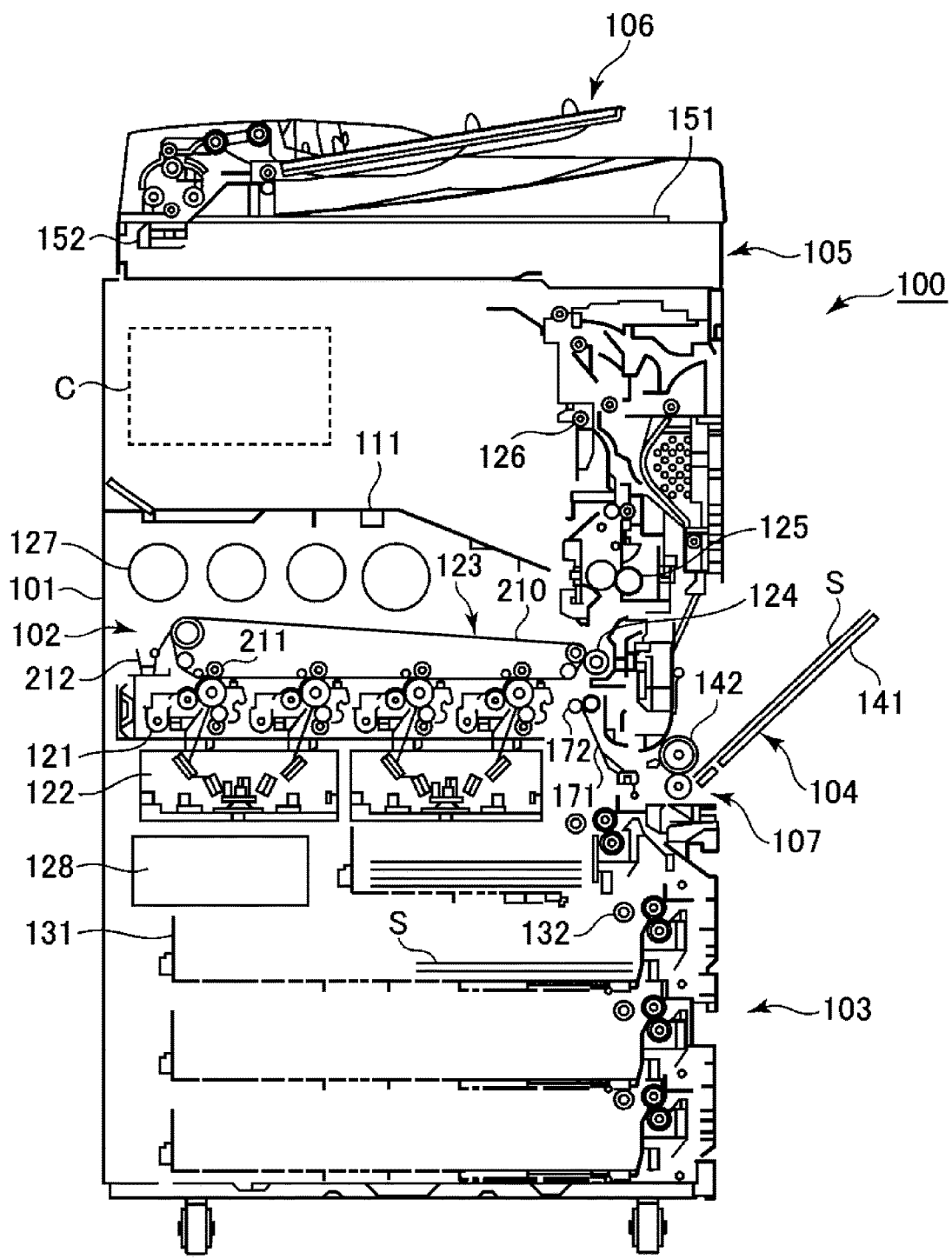
FIG. 1 is a sectional view of an image forming apparatus.

FIG. 1 is a sectional view of an image forming apparatus 100 in this embodiment. The image forming apparatus 100 in this embodiment is a multi-function machine which is capable of forming a full-color image by using an electrophotographic method and which has functions of a copying machine, a printer and a facsimile machine.

Here, as regards the image forming apparatus 100, a front side of the surface of the drawing sheet of FIG. 1 is a "front surface (or front)", and a rear side of the surface of the drawing sheet of FIG. 1 is a "rear (surface) (or back (surface))". A depth direction (front-rear direction) connecting the front side and the rear side of the image forming apparatus 100 is substantially parallel to a rotational axis direction of a photosensitive drum 203 described later. Further, a left-right direction as to the image forming apparatus 100 is a left-right direction in the case where the image forming apparatus 100 is seen from the front side. Further, an up-down direction as to the image forming apparatus 100 refers to an up-down direction, but does not mean only just above and just below, and includes an upper side and a lower side with respect to a horizontal plane passing through a noted element or position. These directions refer to directions in a state in which the image forming apparatus 100 is installed so that the image forming apparatus 100 can be normally used.

The image forming apparatus 100 includes an apparatus main assembly 101. In the apparatus main assembly 101, an image forming portion 102, a sheet feeding device 103, a manual feeding portion 104, an original reading portion 105, a sheet feeding (conveying) portion 107, a controller C and the like are provided.

Figure 2:
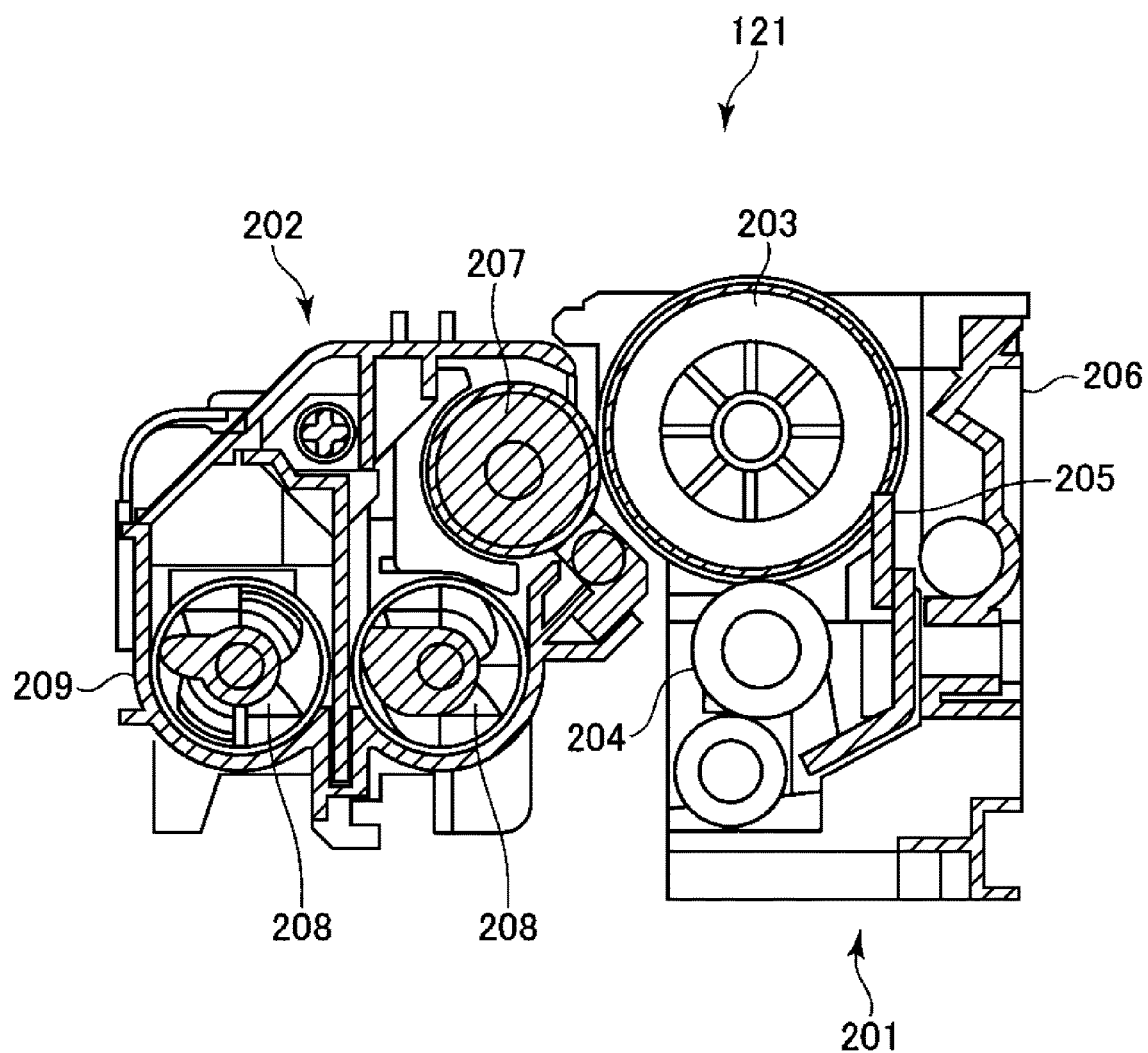
FIG. 2 is a sectional view of a process unit.
Parts (a) and (b) of FIG. 3 are perspective views of the image forming apparatus.

The image forming portion 102 includes a process unit 121, a laser scanner unit 122, an intermediary transfer unit 123, a secondary transfer roller 124, a fixing device 125, a discharging roller 126, a toner cartridge 127, a collecting container 128 and the like. In this embodiment, four process units 121 are provided and arranged substantially in a horizontal direction. These four process units 121 have substantially the same constitution except that colors of toners used for image formation are different from each other. FIG. 2 is a sectional view specifically showing a single process unit 121 as a representative.

The process unit 121 includes a drum unit 201 and a developing unit 202. The drum unit 201 is constituted by a photosensitive drum 203 which is a drum-shaped (cylindrical) photosensitive member (electrophotographic photosensitive member), a charging roller 204, a drum cleaner 205, and a drum unit container 206 for supporting these members. The developing unit 202 is constituted by a developing roller 207, a feeding screw 208, and a developing unit container 209 for supporting these members and accommodating a developer. In this embodiment, the developing unit 202 uses, as the developer, a two-component developer containing toner (non-magnetic toner particles) and a carrier (magnetic carrier particles). The drum unit 201 and the developing unit 202 are individually detachably mountable to the apparatus main assembly 101 by being inserted into and pulled out from the apparatus main assembly 101. The intermediary transfer unit 123 is constituted by an intermediary transfer belt 210 stretched by a plurality of stretching rollers, primary transfer rollers 211 provided in an inner peripheral surface side of the intermediary transfer belt 210 so as to be disposed correspondingly to the respective photosensitive drums 203, and a belt cleaner 212 and the like. In this embodiment, correspondingly to the four predetermined units 121, four toner cartridges 127 are provided and arranged substantially in the horizontal direction. In the toner cartridges 127, toners of yellow (Y), magenta (M), cyan (C) and black (K) are accommodated, respectively. The respective toner cartridges 127 are individually detachably mountable to the apparatus main assembly 101 by being inserted into and pulled out from the apparatus main assembly 101.

The sheet feeding device 103 is constituted by a plurality of sheet accommodating portions 131 as accommodating members for accommodating sheets (transfer materials, recording materials) S such as recording sheets, a feeding roller 132 for feeding the sheets S accommodated in the sheet accommodating portion 131, and the like. The sheet accommodating portion 131 is capable of being pulled out toward the front side of the apparatus main assembly 101.

The manual feeding portion 104 is constituted by a manual feeding tray 141 on which the sheets S are stacked, a manual feeding roller 142 for feeding (sending) the sheet(s) S stacked on the manual feeding tray 141, and the like. The manual feeding tray 141 is provided on a right-hand side surface of the apparatus main assembly 101 so as to be openable. In the case where the manual feeding portion 104 is used, the manual feeding tray 141 is opened and projected to a position where the sheets S are feedable, and the sheets S are stacked on the projected manual feeding tray 141.

Figure 3:
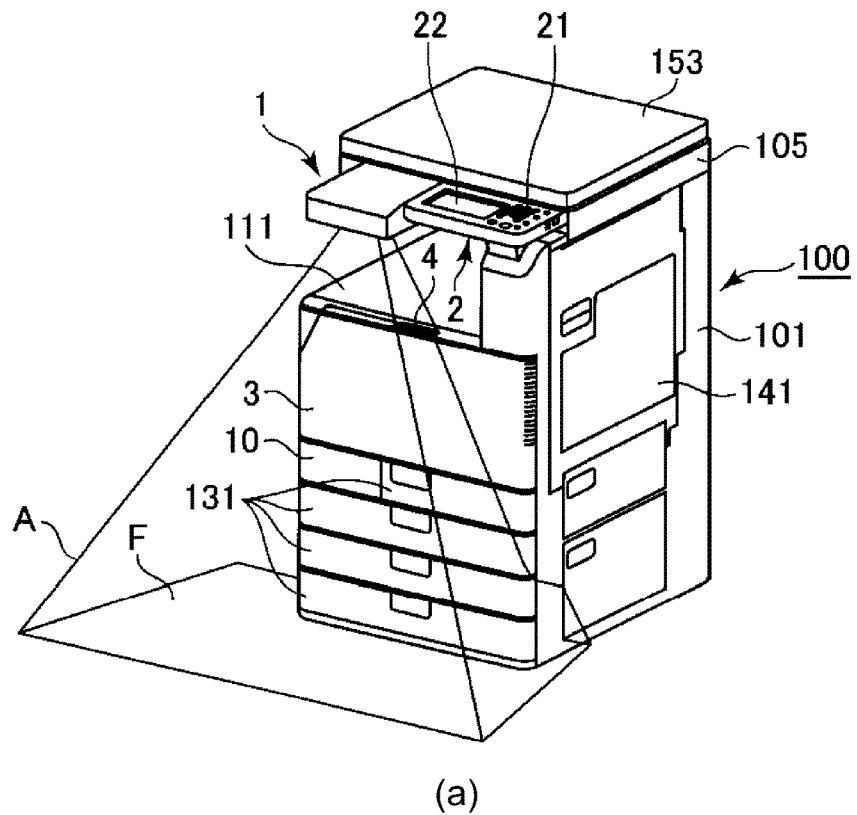
Figure 3:
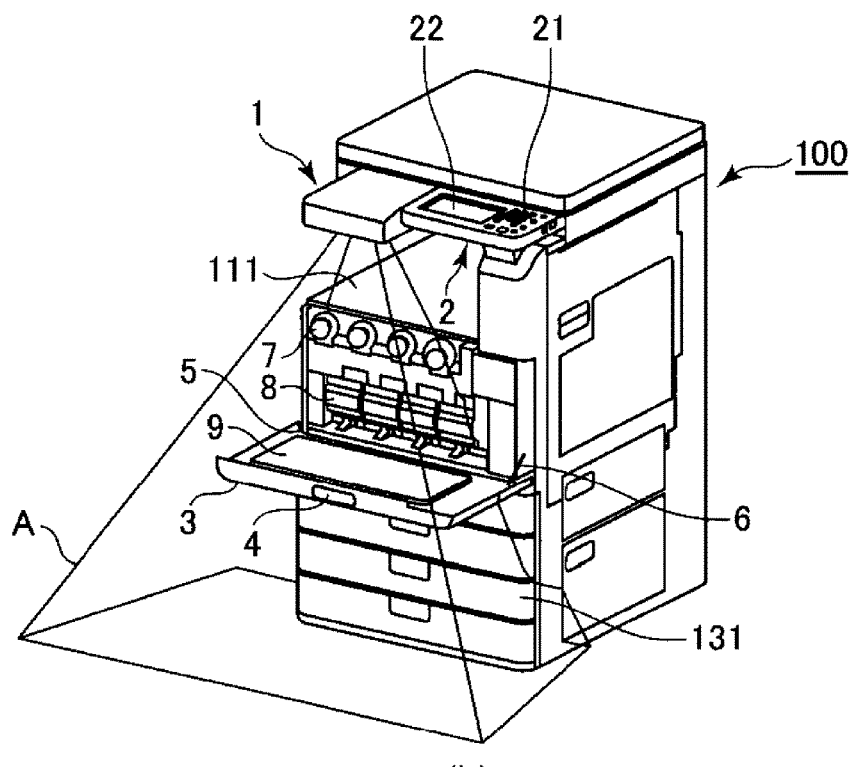
Figure 4:
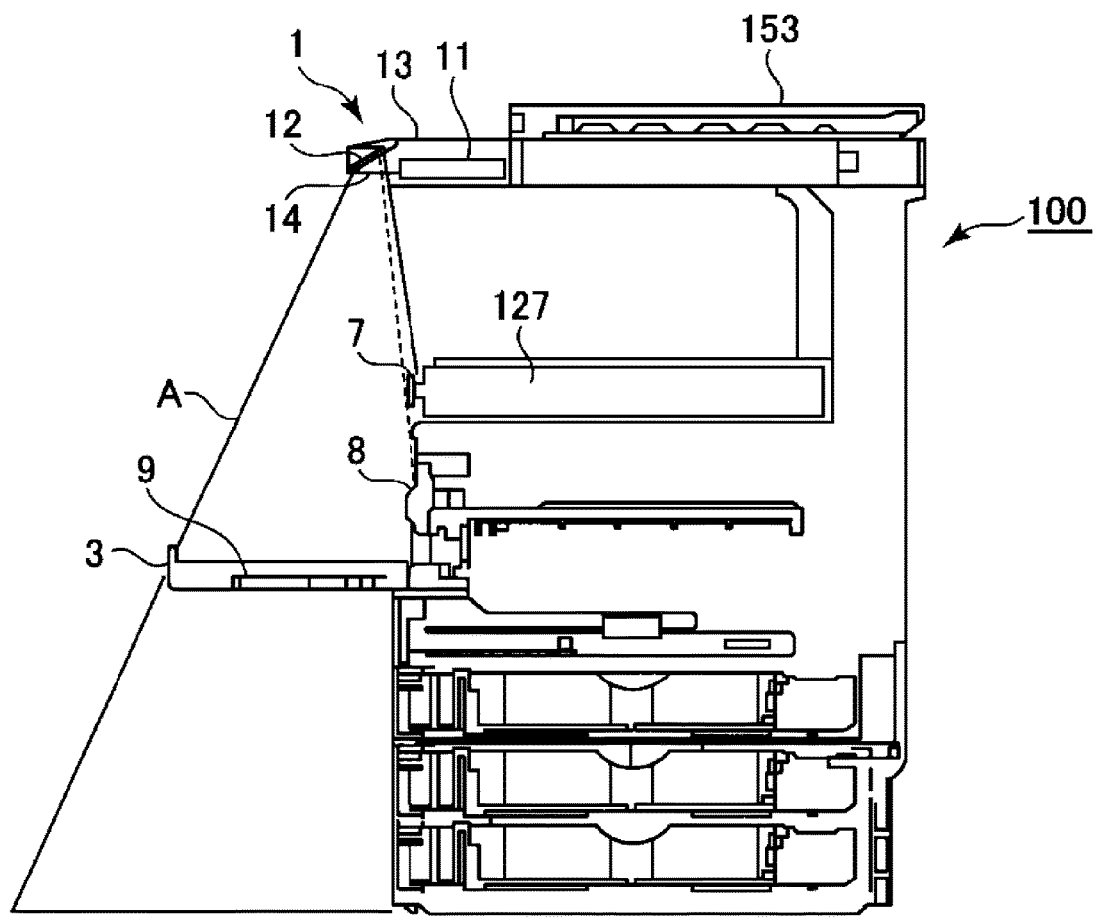
FIG. 4 is a side view of the image forming apparatus.

The original reading portion 105 is constituted by a platen glass 151 as an original carriage, a reading device 152, and the like. The reading device 152 optically reads an original stacked (put) on the platen glass 151 and converts the read data into an electric signal. In FIG. 1, in order to permit continuous reading of a plurality of originals by the reading device 152, at an upper portion of the original reading portion 105, an automatic original (document) feeding device 106 is provided. In FIGS. 3 and 4, a state in which in place of the automatic original feeding device 106, a pressure plate 153 for pressing the original put on the platen glass 151 is mounted is shown.

The sheet feeding portion 107 is constituted by the surface feeding device 103, a sheet feeding path 171 along which the sheet S is sent from the manual feeding portion 104, a registration roller pair 172 for carrying out correction of oblique movement of the sheet S and control of feeding timing of the sheet S, and the like.

The collecting container 128 is a container for collecting the toner discharged as waste from the image forming portion 102. The collecting container 128 is detachably mountable to the apparatus main assembly 101 by being inserted into and pulled out from the apparatus main assembly 101.

In this embodiment, operations of the respective portions of the image forming apparatus 100 are subjected to centralized control by the controller C provided in the apparatus main assembly 101.

2. Image Forming Operation

An image forming operation of the image forming apparatus 100 will be described by taking a copying operation as an example. When an image reading signal is outputted from the controller C to the image reading portion 105, an image of the original is read by the image reading portion 105, and image information is sent to the image forming portion 102. In the image forming portion 102, the surface of the photosensitive drum 203 electrically charged uniformly by the charging roller 204 is irradiated with laser light corresponding to the image information from the laser scanner unit 122, so that an electrostatic latent image (electrostatic image) is formed on the photosensitive drum 203. The electrostatic latent image formed on the photosensitive drum 203 is developed (visualized) by being supplied with the toner by the developing unit 202, so that a toner image is formed on the photosensitive drum 203. The toner image formed on the photosensitive drum 203 is primary-transferred, at a primary transfer portion where the intermediary transfer belt 210 and the photosensitive drum 203 are in contact with each other, onto the intermediary transfer belt 210 by the action of the primary transfer roller 211. For example, during full-color image formation, the toner images of yellow, magenta, cyan and black are successively primary-transferred superposedly from the respective photosensitive drums 203 onto the intermediary transfer belt 210.

On the other hand, when a sheet feeding signal is outputted from the controller C to the sheet feeding device 103, the sheet S is fed from the sheet accommodating portion 131 by the feeding roller 132. When the sheet feeding signal is outputted from the controller C to the manual feeding portion 104, the sheet S is sent from the manual feeding tray 141 by the manual feeding roller 142. Thereafter, the sheet S is conveyed along the sheet feeding path 171, and not only the oblique movement of the sheet S is corrected by the registration roller pair 172 but also the sheet S is timed to the toner images on the intermediary transfer belt 210, and then the sheet S is sent to a secondary transfer portion where the intermediary transfer belt 210 and a secondary transfer roller 124 are in contact with each other.

At the secondary transfer portion, the toner images formed on the intermediary transfer belt 210 are secondary-transferred onto the sheet S by the action of the secondary transfer roller 124. The sheet S on which the toner images are secondary-transferred is heated and pressed by the fixing device 125, so that the toner images are fixed (melt-fixed) on the sheet S. The sheet S on which the toner images are fixed is discharged and stacked by the discharging roller 126 on a discharge tray 111 as a stacking portion provided at an outer portion of the apparatus main assembly 101.

Further, toner (primary transfer residual toner) remaining on the photosensitive drum 203 after a primary transfer step is removed and collected from the photosensitive drum 203 by the drum cleaner 205. Further, toner (secondary transfer residual toner) remaining on the intermediary transfer belt 210 after a secondary transfer step is removed and collected from the intermediary transfer belt 210 by a belt cleaner 212. The toners collected by the drum cleaner 205 and the belt cleaner 212 are accommodated in a collecting container 128 through a collecting toner feeding path (not shown). Further, the image forming portion 102 is provided with a toner hopper (not shown) in which the toner supplied from the toner cartridge 127 is stored and from which the toner in an amount corresponding to an amount of the toner consumed by the development is supplied to the developing unit 202. When the toner in the toner hopper is consumed by the development, the toner is supplied from the toner cartridge 127 to the toner hopper.

3. Operating Portion

An operating portion 2, provided outside the apparatus main assembly 101, for inputting an instruction as the operation of the image forming portion 102 will be described. Parts (a) and (b) of FIG. 3 are perspective views of the image forming apparatus 100 of which a front surface, right side surface and an upper surface are shown, wherein part (a) of FIG. 3 shows a state in which a front door (front cover) 3 described later is closed, and part (b) of FIG. 3 shows a state in which the front door 3 is open. Incidentally, in this embodiment, in a state in which the openable front door 3 is closed and a pullable accommodating member is accommodated, in the case where the image forming apparatus 100 is seen from above, the image forming apparatus 100 has a substantially rectangular shape such that a front side surface and a rear side surface are substantially parallel to each other and that a left side surface and a right side surface are substantially parallel to each other.

In this embodiment, the image forming apparatus 100 includes, on the front side surface, particularly on the front side surface of the image reading portion 105, the operating portion 2 for permitting input of various settings such as a process condition of the sheet S, a start instruction of the image forming operation, and the like to the controller C. In this embodiment, the operating portion 2 is provided so as to project from the front side surface of the image reading portion 105 toward the front side.

The operating portion 2 is constituted by buttons (switches) 21 as input means for permitting input of instructions to the controller C, and a display (liquid crystal screen) 22 as a display means for displaying information for an operator such as a user or a maintenance person. In this embodiment, the display 22 is constituted by a touch panel and also has a function of an input means. The operator operates, in general, the operating portion 2 from the front side of the image forming apparatus 100, so that the operator can input necessary items to the controller C and can cause the image forming apparatus 100 to start the image forming operation.

Further, the image forming apparatus 100 is configured so that the operator can perform maintenance (exchange) from the front side of the image forming apparatus 100 where the operating portion 2 is provided. That is, on the front side surface of the image forming apparatus 100, the front door 3 as a door member openable for exposing at least a part of the image forming portion 102 to the outside of the image forming apparatus 100 is provided. The front door 3 is provided with a front door grip 4 gripped by the operator when the operator opens and closes the front door 3. The front door 3 is rotatably connected with the apparatus main assembly 101 by a hinge 5.

The front door 3 is opened by being rotated from above toward below about a rotational axis crossing the vertical direction and is closed by being rotated from below toward above about the rotational axis. Particularly, in this embodiment, the front door 3 is opened by being rotated from above toward below about a rotational axis (horizontal direction hinge) substantially parallel to the horizontal direction and is closed by being rotated from below toward above about the rotational axis (horizontal direction hinge). Here, "substantially parallel to the horizontal direction" includes not only the case where the rotational axis is completely parallel to the horizontal direction, but also the case where the rotational axis is deviated from the parallel direction within a degree of an error (e.g., within ±10 degrees). Typically, as in this embodiment, a constitution in which the front door 3 is opened and closed by being rotated about the rotational axis substantially parallel to the horizontal direction is employed. However, even when the rotational axis has a certain angle (45 degrees or less, preferably 30 degrees or less) with respect to the horizontal direction, an effect similar to the effect of this embodiment can be obtained.

When the front door 3 is opened, the front door 3 is locked to the apparatus main assembly 101 by a locking tool 6. Inside the front door 3, a front door projection portion 9 on which the operation guidance is projected by a projector unit 1 described later. In this embodiment, the front door projection portion 9 is constituted by an inside surface of the front door 3 itself, but may also be a member mounted on the inside portion of the front door 3. In a state in which the front door 3 is opened and is locked to the apparatus main assembly 101, an angle of a surface of the front door projection portion 9 formed with respect to a projection optical axis of the projector unit 1 is maintained at a predetermined angle (this angle will be specifically described in Embodiment 2).

When the front door 3 is opened, end portions of the toner cartridges 127 in the front side and small doors 8 for exposing end portions of the process units 121 in the front side to an outside of the image forming apparatus 100 are exposed to the outside of the image forming apparatus 100. In this embodiment, four toner cartridges 127 and four small doors 8 are provided and arranged substantially in the horizontal direction correspondingly to four process units 121. Each of the toner cartridges 127 can be mounted into and demounted from the apparatus main assembly 101 by being inserted into and pulled out from the apparatus main assembly 101 in the front-rear direction by operating a cartridge grip 7 provided at the end portion thereof in the front side. Further, by opening the small door 8, the drum unit 201 and the developing unit 202 can be mounted into and demounted from the apparatus main assembly 101 by being individually inserted into and pulled out from the apparatus main assembly 101 in the front-rear direction. The small door 8 is opened by being rotated from above toward below about a rotational axis substantially parallel to the horizontal direction, and is closed by being rotated from below toward above about the rotational axis. In this embodiment, the small door 8 also functions as a lever as a portion-to-be-operated for changing the state of the drum unit 201 and the developing unit 202 between a detachably mountable state and a set state.

4. Projector Unit

Next, a projecting portion for projecting the operation guidance (guidance display, guiding display) will be described. FIG. 4 is a sectional view of the image forming apparatus 100, as seen from the right side, in a state in which the front door 3 is open. In this embodiment, the case where the operation guidance regarding an operation for exchanging the toner cartridge 127 by the operator is projected on the front door projection portion 9 by the projecting portion when the operation is performed by the operator will be described as an example.

As shown in FIGS. 3 and 4, in this embodiment, the image forming apparatus 100 includes the toner cartridges 127 as objects-to-be-operated provided in the apparatus main assembly 101 so as to oppose the front door 3 in a state in which the front door 3 is closed. Further, in this embodiment, the image forming apparatus 100 includes the projector unit 1 as the projecting portion for projecting the operation guidance regarding the toner cartridges 127, in the state in which the front door 3 is open, from above onto the front door projection portion 9 provided inside the front door 3. In this embodiment, when a side surface side where the operating portion 2 is disposed is the front side of the image forming apparatus 100, the front door 3 is provided in the front side of the image forming apparatus 100. Incidentally, the projection from above is not limited to projection from above toward below in the vertical direction, but may also include projection from above toward below with an angle with respect to the vertical direction. For example, in the case where the image forming apparatus 100 is seen from the front side, the projection may also be carried out from the upper left toward the lower right or from the upper right toward the lower left, and in the case where the image forming apparatus 100 is seen from the right side, the projection may also be carried out from the upper rear toward the lower front or from the upper front toward the lower rear. Further, the operation guidance may also be in any form such as illumination, characters, symbols, figures (diagrams), still images (pictures) or moving images (animation), for instructing or illustrating an operating portion, an operating direction, an operating method or the like.

In this embodiment, the projector unit 1 is provided on the side surface of the image forming apparatus 100 at the front side, particularly on the side surface of the image reading portion 105. In this embodiment, the projector unit 1 is projected so that at least a part thereof projects from the side surface at the front side of the image reading portion 105 toward the front side. The projector unit 1 is constituted by a projector 11, a reflection mirror 12 and a projector cover 13 for accommodating these members and is provided with a projection opening 14 formed at a lower portion of the projector cover 13. Light is projected toward below through the projection opening 14, so that the operation guidance is projected onto the object-to-be-projected provided in a projectable region A, particularly onto the front door projection portion 9 provided inside the front door 3 in this embodiment. In this embodiment, a projection axis (optical axis of a projection image projected through the projection opening 14) of the projector unit 1 extends below substantially in the vertical direction. Here, "extends below substantially in the vertical direction" includes not only the case where the optical axis extends below completely in the vertical direction, but also the case where the optical axis extends in a direction deviated from vertically below within a range of an error (for example, ±about 10 degrees).

5. Exchanging Operation of Toner Cartridge

Figure 10:
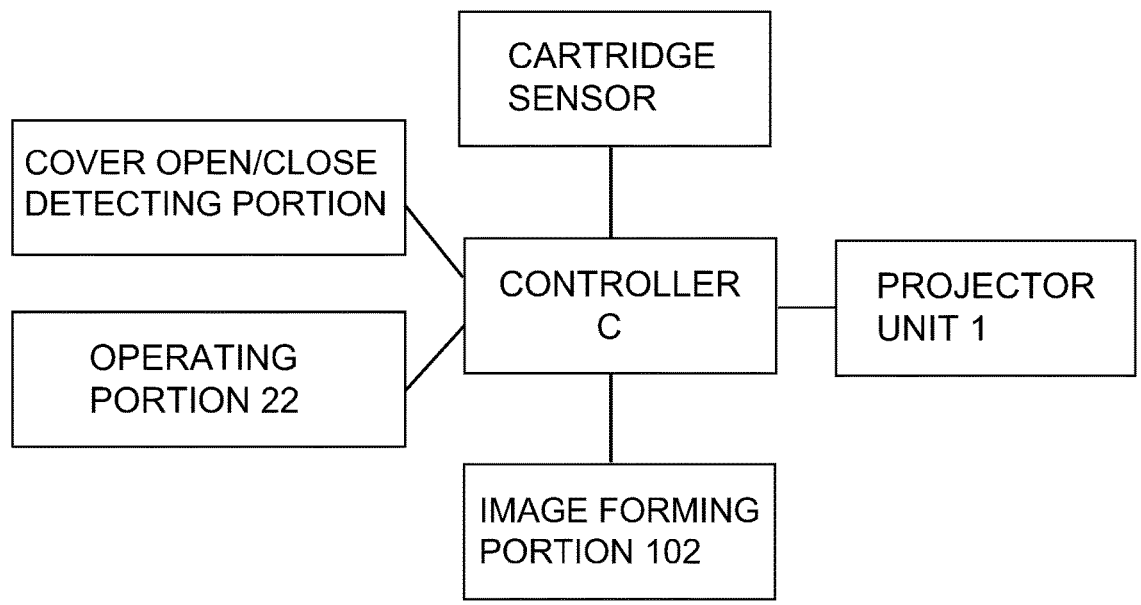
FIG. 10 is a block diagram of an embodiment of the present invention.

First, a block diagram in this embodiment will be described with reference to FIG. 10. A controller C controls the operation of the image forming portion 102, and effects control as to contents displayed at the operating portion 22. Further, the controller C controls an operation of the projector unit 1 by input from a cover opening/closing detecting portion and input from a cartridge presence/absence sensor.

In this embodiment, in the case where a small remaining toner amount in the toner cartridge 127 is detected, a message prompting the operator to exchange the toner cartridge 127 is displayed on the display (operating portion) 22. Incidentally, similar contents may also be projected by the projector unit 1 onto the surface of a floor, at the front side of the image forming apparatus 100, where the image forming apparatus 100 is installed. Then, when the front door 3 is opened by the operator, the cover opening/closing detecting portion detects the opening of the front door 3, and the operation guidance as to the exchange operation of the toner cartridge 127 is projected onto the front door projection portion 9 by the projector unit 1.

The front door 3 is opened by being rotated through the hinge 5 from above toward below about the rotational axis substantially parallel to the horizontal direction. Then, by the locking tool 6, the surface of the front door 3 is locked to the apparatus main assembly 101 so that an angle of the surface of the front door projection portion 9 with respect to the projection optical axis of the projector unit 1 is maintained at a predetermined angle. For that reason, the operator performing the operation from the front side of the image forming apparatus 100 is capable of making reference to the operation guidance in contrast with the toner cartridge 127 while satisfactorily visually recognizing the toner cartridge 127, which is the object-to-be-operated. This will be further described specifically.

Figure 5:
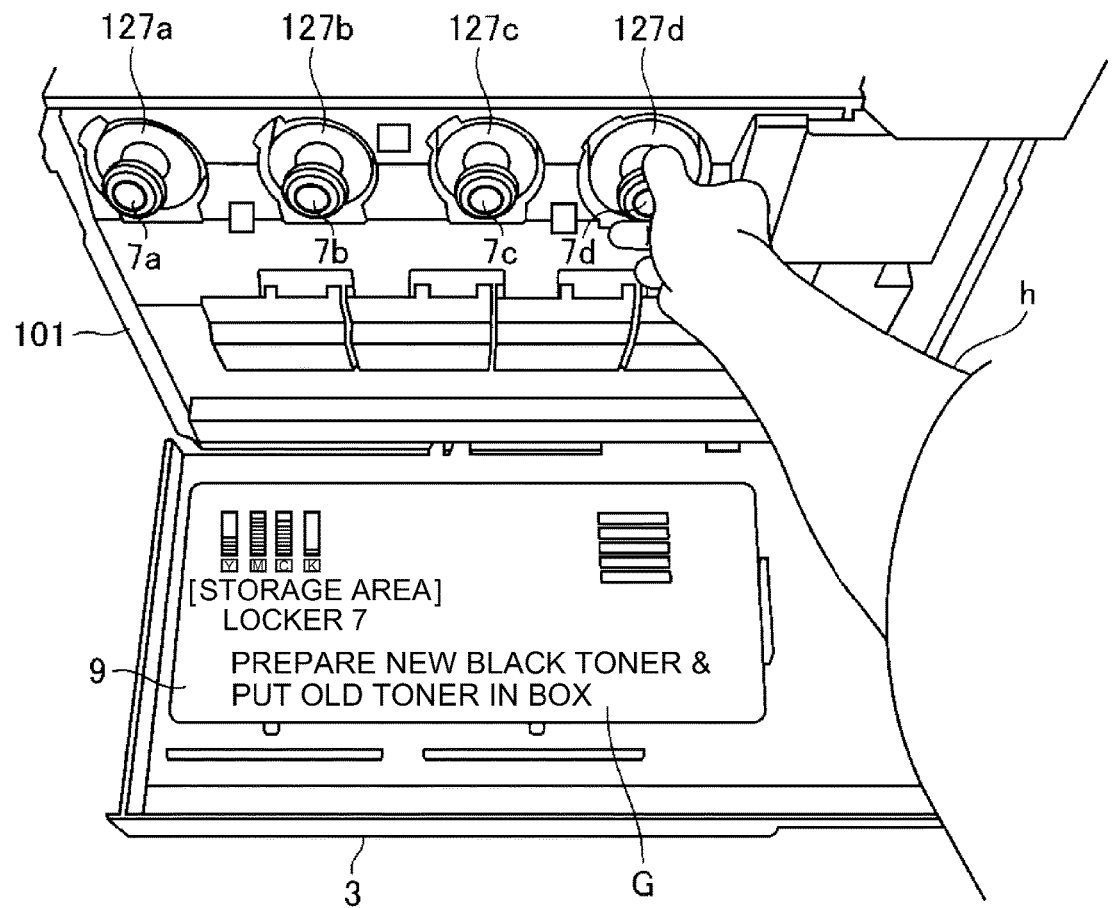
FIG. 5 is a schematic view in the neighborhood of a front door projection portion as seen from an operator.

FIG. 5 is a schematic view showing the neighborhood of the front door projection portion 9 and the toner cartridges 127 when the apparatus main assembly 101 is seen by the operator performing the operation from the front side of the image forming apparatus 100. As shown in FIG. 5, operation guidance G is projected onto the front door projection portion 9 by the projector unit 1. In an example of FIG. 5, the right end toner cartridge (for black in this embodiment) 127d is the toner cartridge as the object-to-be-exchanged at this time. The left-side three toner cartridges 127a, 127b and 127c are toner cartridges which are not the object-to-be-exchanged at this time. In FIG. 5, also a hand h of the operator is shown.

The front door 3 is opened by being rotated from above toward below about the rotational axis substantially parallel to the horizontal direction, and therefore, the operation guidance G projected onto the front door projection portion 9 is to be displayed in the neighborhood of the object-to-be-operated (for example, the toner cartridge 127d during pulling-out) as seen from the operator.

Accordingly, the operator is capable of making reference to the operation guidance G in contrast with the toner cartridge 127d while satisfactorily visually recognizing the toner cartridge 127d which is the object-to-be-operated.

Figure 6:
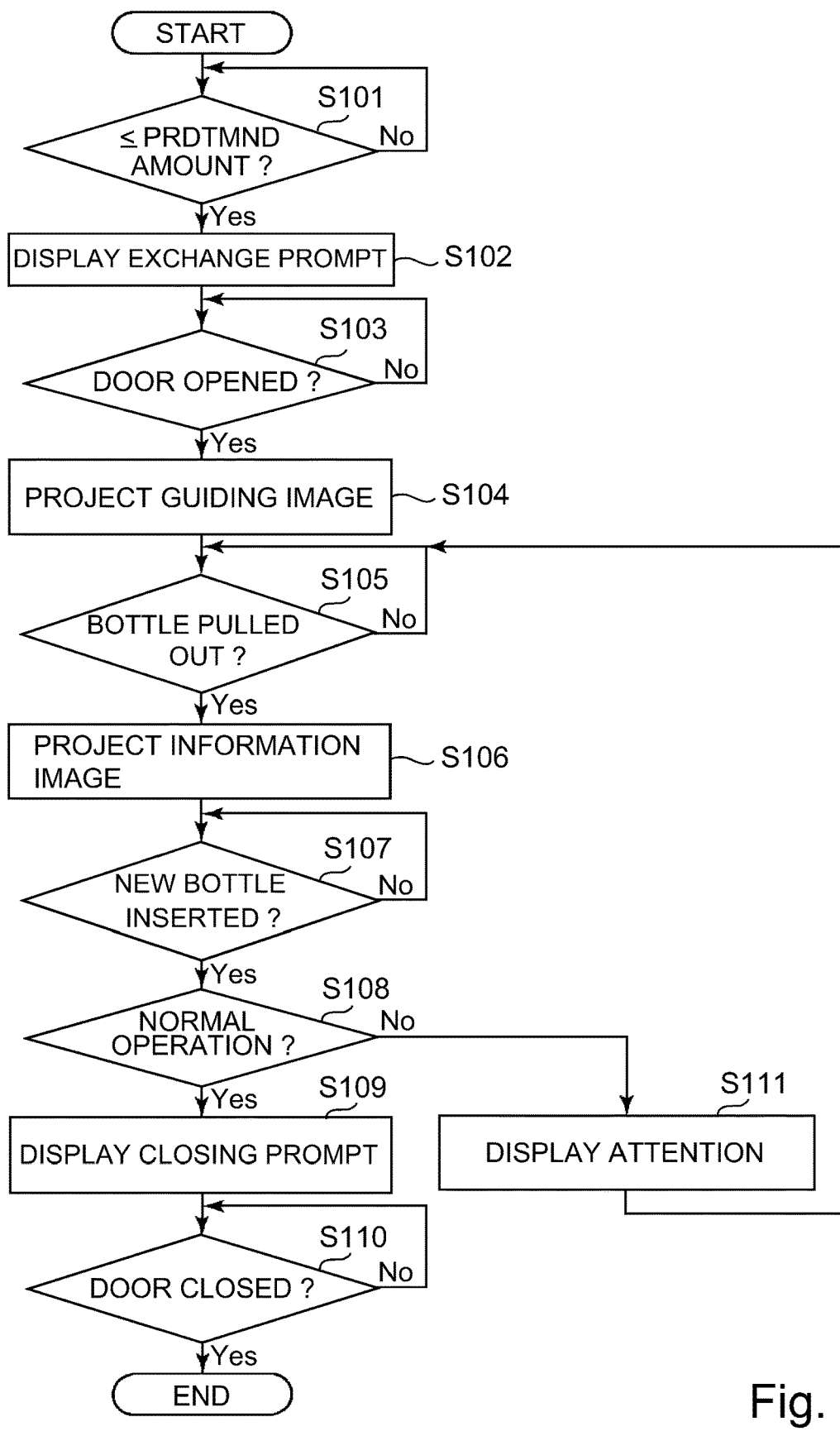
FIG. 6 is a flowchart of an operation for displaying operation guidance as to an exchange operation of a toner cartridge.
Parts (a) to (c) of FIG. 7 are schematic views each showing the operation guidance as to the exchange operation of the toner cartridge.
Parts (a) and (b) of FIG. 8 are schematic views for illustrating an angle of opening of a front door.
Parts (a) to (d) of FIG. 9 are schematic views showing a difference in vision of the operation guidance depending on the angle of opening of the front door.

FIG. 6 is a flowchart showing a flow of an operation for displaying the operation guidance as to the exchange operation of the toner cartridge 127 in this embodiment.

The controller C discriminates whether or not detection that the remaining toner amount in the toner cartridge 127 is not more than a predetermined amount is carried out by the remaining toner amount sensor (S101). When the detection that the remaining toner amount in any one of the toner cartridges is not more than the predetermined amount is carried out, the controller C causes the display 22 of the operating portion 2 to display a message for prompting the operator to exchange the associated toner cartridge 127 (S102). Next, the controller C discriminates whether or not detection that the front door 3 is opened is carried out by the opening/closing sensor (not shown) provided in the apparatus main assembly 101 (S103). When the detection that the front door 3 is opened is carried out, the controller C causes the projector unit 1 to project, onto the front door projection portion 9, the operation guidance G for illustrating the exchanging method of the toner cartridge 127 (S104). At this time, in order to clear the toner cartridge 127 as the object-to-be-exchanged, the operation guidance can be displayed in a region (which overlaps with the toner cartridge 127 with respect to the left-right direction as seen from the front side), of the front door projection portion 9, corresponding to the toner cartridge 127 as the object-to-be-exchanged.

Next, the controller C discriminates whether or not detection that the toner cartridge 127 is pulled out from the apparatus main assembly 101 is carried out by the cartridge presence/absence sensor provided in the apparatus main assembly 101 (S105). When the pulling-out of the toner cartridge 127 is detected, the controller C switches the contents of the operation guidance to display for prompting the operator to insert a new toner cartridge 127 (S106). At this time, in order to easily put the operation guidance G in contrast with the toner cartridge 127 as the object-to-be-exchanged, the operation guidance G can be projected while avoiding a region (which overlaps with the toner cartridge 127 with respect to the left-right direction as seen from above) in which the toner cartridge 127 as the object-to-be-exchanged is pulled out.

Then, the controller C discriminates whether or not detection that the toner cartridge 127 is inserted to a predetermined position is carried out by the above-described cartridge presence/absence sensor (S107). When the insertion of the toner cartridge 127 is detected, the controller C discriminates whether or not the operation is normally performed (S108). At this time, in this embodiment, information stored in a storing portion provided on the toner cartridge 127 is inputted to the controller C, so that whether or not the used-up toner cartridge 127 or the toner cartridge 127 different in color is inserted is checked. In the case where the operation is normally performed, the controller C switches the contents of the operation guidance G to display for prompting the operator to close the front door 3 (S109).

Then, when the closing of the front door 3 is detected by the above-described opening/closing sensor (S110), the controller C ends the operation for displaying the operation guidance as to the exchange operation of the toner cartridge 127. On the other hand, in S108, discrimination that the operation is not normally performed is made, the controller C switches the contents of the operation guidance G to attention display for notifying the operator of the discrimination to that effect (S111), and then returns the process to S105.

Figure 7:
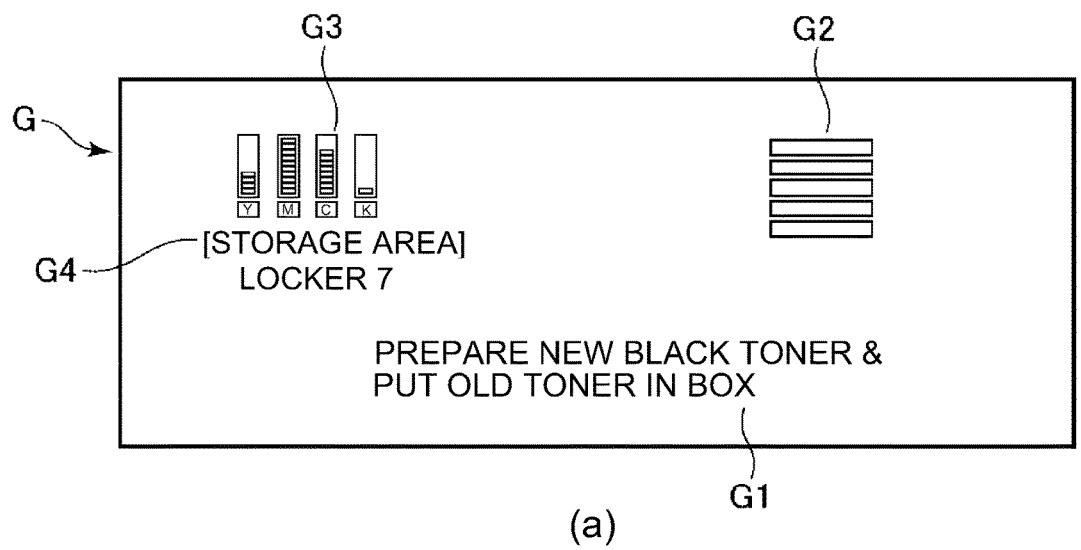
Figure 7:
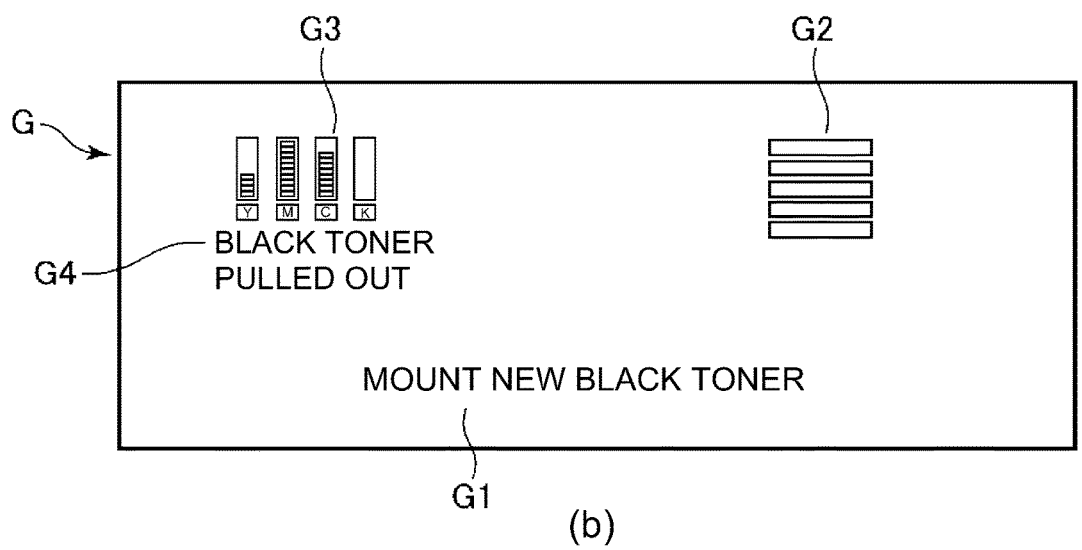
Figure 7:
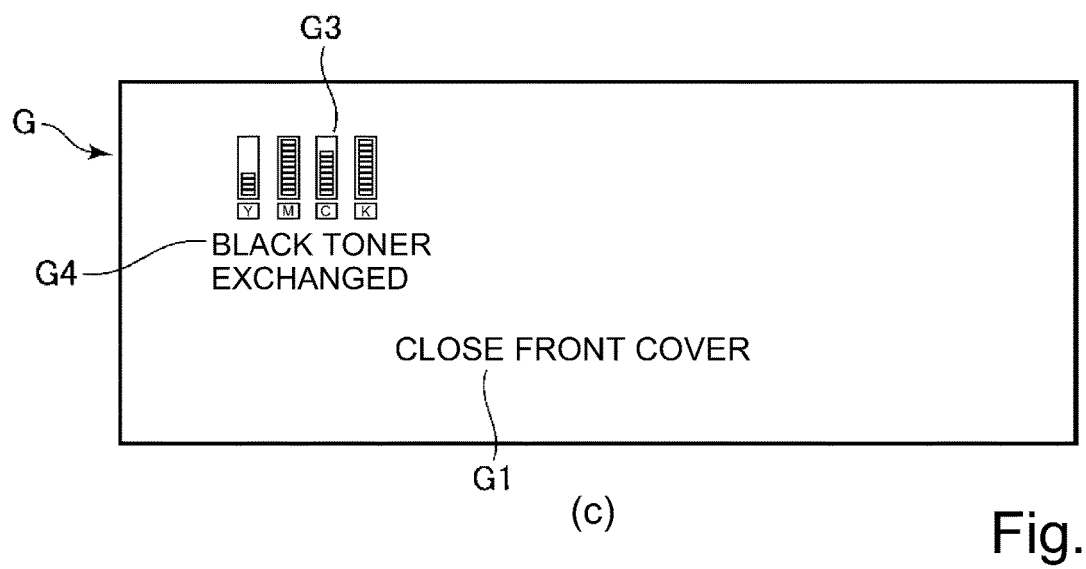

Parts (a) to (c) of FIG. 7 are schematic views each showing an example of the contents of the operation guidance G switched on the basis of a result of detection of the opening/closing of the front door 3, the insertion/pulling-out of the toner cartridge 127, or the like.

In this embodiment, when the opening of the front door 3 is detected, the operation guidance G of part (a) of FIG. 7 is displayed. The operation guidance G of part (a) of FIG. 7 includes a message G1 illustrating an operation method, a figure G2 showing an operation portion, a figure G3 showing a remaining toner amount and the like, a sub-message G4, and the like. When the pulling-out of the toner cartridge 127 is detected, the operation guidance G of part (b) of FIG. 7 is displayed. In the operation guidance G of part (b) of FIG. 7, the message G1 illustrating the operation method is changed to a display prompting the operator to insert a new toner cartridge 127. Then, when the insertion of the new toner cartridge 127 to a predetermined position is detected, the operation guidance G of part (c) of FIG. 7 is displayed. In the operation guidance G of part (c) of FIG. 7, the message G1 illustrating the operation method is changed to a display prompting the operator to close the front door 3.

As described above, according to this embodiment, it becomes possible to make reference to the operation guidance in contrast with the toner cartridge 127 while satisfactorily visually recognizing the toner cartridge 127 disposed in the apparatus main assembly 101 so as to oppose the front door 3 in a state in which the front door 3 is closed.

Embodiment 2

Another embodiment of the present invention will be described. A basic structure and a basic operation of an image forming apparatus in this embodiment are the same as those of the image forming apparatus in Embodiment 1. Accordingly, in the image forming apparatus in this embodiment, elements having the same or corresponding functions or structures as those of the image forming apparatus in Embodiment 1 are represented by the same reference numerals or symbols as in Embodiment 1 and will be omitted from detailed description.

In this embodiment, an example of a change of an angle of the surface of the front door projection portion 9 formed with respect to a projection optical axis in a state in which the front door 3 is opened and locked to the apparatus main assembly 101 will be described. The angle is represented by an angular unit ("°" or "degrees") in a degree measure, and 90° is equal to a right angle.

Figure 8:
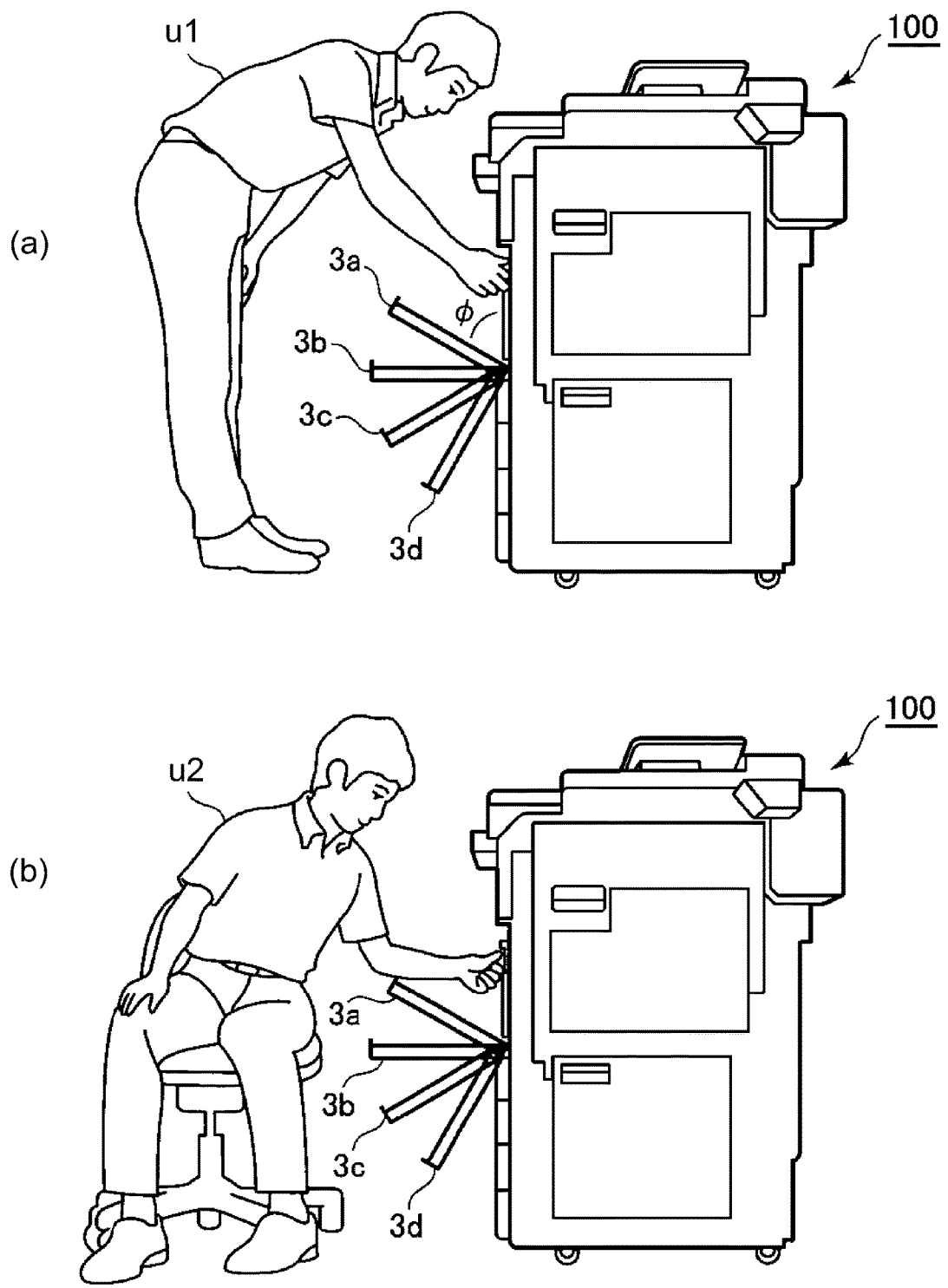

Parts (a) and (b) of FIG. 8 are schematic views each showing the image forming apparatus 100 as seen from the right side and the operator performing an operation such as exchange of the toner cartridge 127. Part (a) of FIG. 8 shows an operator u1 in a standing position, and part (b) of FIG. 8 shows an operator u2, in a sitting position, such as a user in a wheelchair. In this embodiment (ditto for Embodiment 1), it is assumed that an eye point, during the operation, of each of the operator u1 in the standing position and the operator u2 in the sitting position is equal to a height of the operating portion 2.

An angle φ in part (a) of FIG. 8 is an open angle (angle of an opening) of the front door 3. In part (a) of FIG. 8, front doors 3a, 3b, 3c and 3d in states that the front doors are opened with open angles φ=60°, φ=90°, φ=120° and φ=150°, respectively, and are locked to the apparatus main assembly 101 are shown.

Here, in the case where the projection from the projector unit 1 is carried out downwardly substantially in the vertical direction, the angle θ of the surface of the front door projection portion 9 formed with respect to the projection optical axis is substantially equal to the open angle φ. That is, when φ=90°, θ=90° holds, and an incident direction and a reflection direction of a projection light flux are equal to each other, so that an entirety of the projection surface is substantially uniformly irradiated with the projection light flux.

On the other hand, in the case where the open angle φ is not 90°, a distance from the projector unit 1 to an end portion of the front door 3 at the hinge 5 side with respect to the front-rear direction and a distance from the projector unit 1 to the other end portion (open/close end) at a side opposite from the hinge 5 with respect to the front-rear direction are different from each other. For that reason, when either one of these end portions is properly irradiated with the projection light flux, in another end portion side, a light quantity is excessive or insufficient, so that a difference in brightness at the display portion generates.

Incidentally, the front door 3 is originally opened for maintenance, exchange or the like of members, accommodated inside the front door 3, such as the sheet feeding portion 107, the toner cartridges 127, the drum units 201, and the developing units 202. For that reason, when the open angle φ of the front door 3 is less than 90°, for example, the pulling-out direction of the toner cartridge 127 is blocked, and thus operativity lowers.

Figure 9:
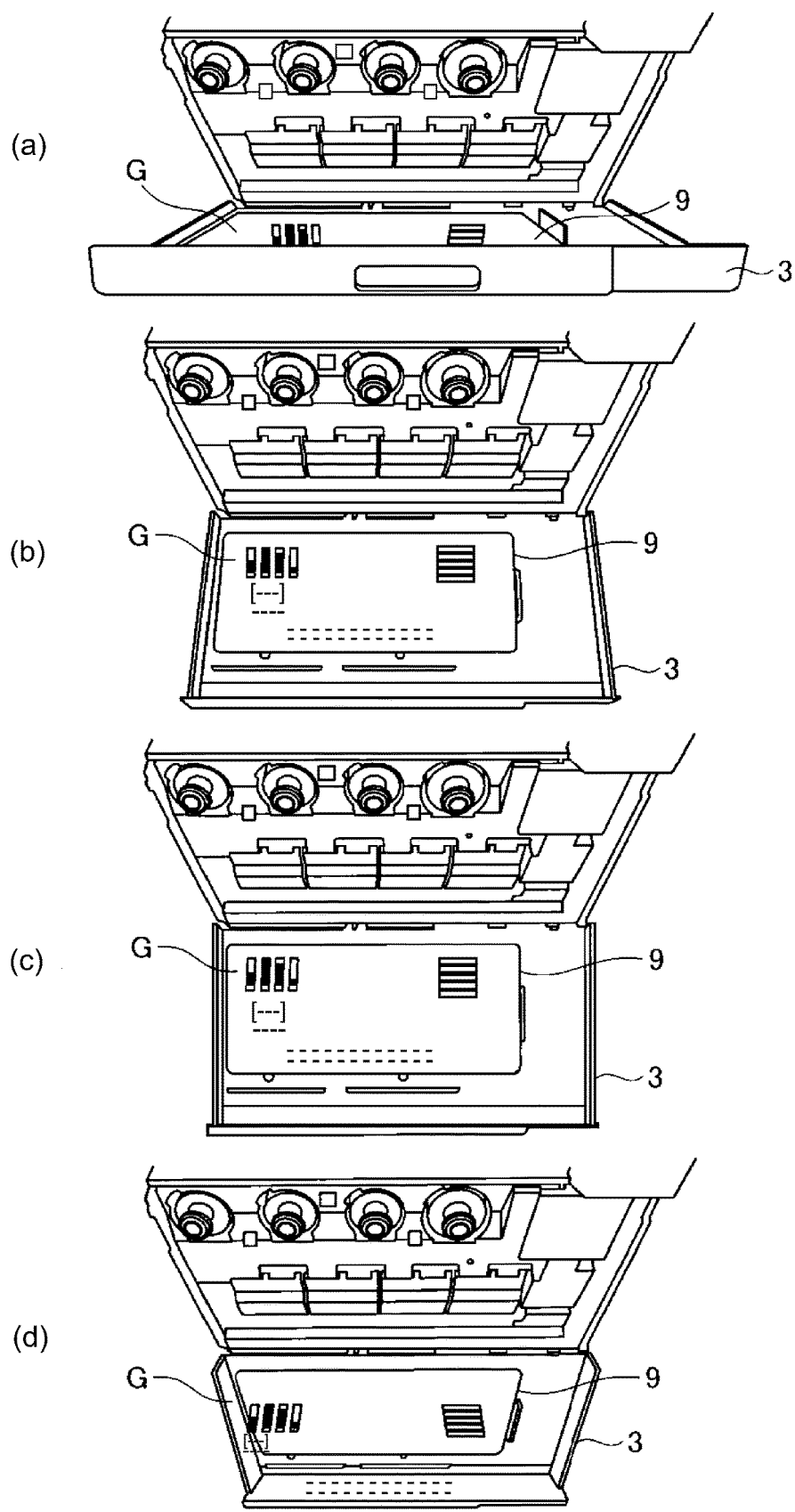

Parts (a) to (d) of FIG. 9 are schematic views showing a difference in field of vision of the operation guidance G from the eye points of the operators u1 and u2 in the case where the open angle φ is changed. Parts (a) to (d) of FIG. 9 show the fields of vision of the operation guidance G on the front doors 3a, 3b, 3c and 3d, respectively, in states that the front doors are opened with the open angles θ=60°, θ=90°, θ=120° and θ=150°, respectively, and are locked to the apparatus main assembly 101.

Table 1 appearing hereinafter shows an evaluation result from viewpoints of operativity and viewability at the respective open angles φ of the front doors 3. The operativity is evaluated by whether or not a demounting operativity of the toner cartridge 127 is good, wherein the operativity was evaluated as "○" when the operativity was good and was evaluated as "x" when the operativity was not good. Further, as regards the viewability, the following items (1) to (3) were evaluated. In the item (1), whether or not a difference in brightness of the operation guidance G is sufficiently small between the hinge 5 side and its opposite side of the front door projection portion 9 was evaluated. In the item (2), whether or not a sufficient region for displaying the operation guidance G is ensured for the operators u1 and u2 at the front door projection portion 9 was evaluated. In the item (3), a degree of distortion of display (trapezoidal distortion) due to a difference in distance from the projector unit 1 to the front door projection portion 9 was evaluated. As regards the brightness difference, the brightness difference was evaluated as "○" when the brightness difference was sufficiently small and thus the operation guidance G was easily recognized, and was evaluated as "x" when the brightness difference was large to the extent that the operation guidance G was not readily recognized. As regards the display region, the display region was evaluated as "○" when a sufficient region capable of displaying the operation guidance G in contrast with the object-to-be-operated was able to be ensured, and was evaluated as "x" when the sufficient region was unable to be ensured. As regards the trapezoidal distortion, the trapezoidal distortion was evaluated as "○" when the trapezoidal distortion was sufficiently small and thus the operation guidance G was easily recognized, and was evaluated as "x" when the trapezoidal distortion was large to the extent that the operation guidance G was not readily recognized.

TABLE 1

| Open Angle | Operativity*1 | Viewability*2 | | |
|---|---|---|---|---|
| | | BD*3 | DR*4 | TD*5 |
| 60° | X (C1) | X (C2) | X (C3) | X (C4) |
| 90° | ○ | ○ | ○ | ○ |
| 120° | ○ | ○ | ○ | ○ |
| 150° | ○ | X (C2) | X (C3) | X (C4) |

*1"X (C1)" was that demounting of an accommodated member was blocked.
*2"X (C2)" was that the degree of the brightness difference was large.
"X (C3)" was that the sufficient region was not ensured.
"X (C4)" was that the degree of the distortion was large.
*3"BD" was the brightness difference.
*4"DR" was the display region.
*5"TD" was the trapezoidal distortion.

As shown in Table 1, in the cases of φ=90° and φ=120°, all of the evaluation items were evaluated as good ("○"), but in the cases of φ=60° and φ=150°, there were evaluation items evaluated as no-good ("x"). Further, when evaluations similar to the above-described evaluations were repeated while changing the open angle φ between 120° and 150°, it turned out that all of the evaluation items were evaluated as good until φ=135°.

Thus, the angle θ of the front door projection portion 9 formed with respect to the projection optical axis of the projector unit 1 when the front door 3 is opened and is locked to the apparatus main assembly 101 may preferably be 90° or more and 135° or less, more preferably be 90° or more and 120° or less. By setting the angle θ at the above range, it is possible to perform the operation of the object-to-be-operated, disposed so as to oppose the front door 3 in the state that the front door 3 is closed, while making reference to the operation guidance G displayed on the front door projection portion 9 with good operativity and good viewability.

Embodiment 3

Another embodiment of the present invention will be described. A basic structure and a basic operation of an image forming apparatus in this embodiment are the same as those of the image forming apparatus in Embodiment 1. Accordingly, in the image forming apparatus in this embodiment elements having the same or corresponding functions or structures as those of the image forming apparatus in Embodiment 1 are represented by the same reference numerals or symbols as in Embodiment 1 and will be omitted from detailed description.

In this embodiment, an example of a change in smoothness of the front door projection portion 9 will be described.

When a resin material such as plastics is subjected to molding or press working, a process of subjecting the surface of the resin material to minute unevenness (projections and recesses) is called "embossing process". Further, such a pattern itself is also referred to as "embossing". The "embossing" has an effect of sense of beauty such that contamination or damage with finger print is made inconspicuous and an effect of operativity such as slipping (skidding) prevention, and therefore, in the image forming apparatus, a surface of an outer casing and a surface of an operating member such as a grip are subjected to the embossing (process) in general.

Incidentally, in this embodiment (ditto for Embodiments 1 and 2), the inside surface of the front door 3 is used as a projection screen (the front door projection portion), and therefore, it is desired that the surface is constituted so as to be smooth without providing a rigid material which is a so-called rib. However, when the surface is made smooth to the extent that a difference in unevenness (distance from a top of a projected portion to a bottom of a recessed portion) PV is less than 0.01 mm (PV<0.01 mm), the viewability lowers in some cases due to the following causes (1) and (2). Due to the cause (1), the difference in brightness generates between display in the neighborhood of a center portion of the projection optical axis and display at a peripheral portion. Due to the cause (2), when an external light source such as indoor light is provided along the same direction as the projection optical axis, an image of light from the external light source becomes excessively clear on the projection screen.

Therefore, it is preferable that at least a part of the surface, of the inside portion of the front door 3, where the operation guidance is projected is a minute uneven surface provided with unevenness for diffusing the light from the projector unit 1. In this embodiment, a substantially entire surface of the front door projection portion 9, provided inside the front door 3, onto which the operation guidance is projected is the minute uneven surface.

The unevenness of the minute uneven surface can be appropriately set so as to achieve the following effects (1) and (2). The effect (1) is such that the projected light is reflected and diffused and thus generation of the brightness difference exceeding a tolerable range between the display in the neighborhood of the center portion of the projection optical axis and the display at the peripheral portion can be suppressed. The effect (2) is such that even in the case where an external light source such as indoor lighting is provided along the same direction as the projection optical axis, it is possible to alleviate a degree of prevention of the viewability of the operation guidance due to the clear image of the light from the external light source on the projection screen. According to a study by the present inventors, it turned out that a good result can be obtained by constituting the front door projection portion 9 with a resin material having the minute uneven surface providing the unevenness difference of 0.01 mm<PV<1 mm. In this embodiment, the minute uneven surface is formed by the above-described embossing (process).

In some cases, an optical characteristic similar to the above-described optical characteristic can be obtained by, for example, a method such that a special pigment is applied onto the screen surface. However, according to the method in which the surface of the front door projection portion 9 is subjected to the embossing, the above-described optical characteristic can be obtained by a relatively simple method similar to the method of subjecting, to the embossing, the surface of the outer casing of the image forming apparatus and the surface of the operating member such as the grip, and thus such a method is advantageous.

In this embodiment, the inside surface of the front door 3 itself is used as the projection screen, but in the case were a member functioning as the projection screen is mounted to the inside surface of the front door 3, the minute uneven surface may only be formed on this member.

Other Embodiments

In the above, the present invention was described based on specific embodiments, but is not limited to the above-described embodiments.

As the object-to-be-operated disposed in the apparatus main assembly so as to oppose the inside surface of the door member in the state that the door member is closed, in addition to the toner cartridge described as an example in the above-described embodiments, for example, it is possible to cite the following members. The drum unit 201, the developing unit 202 and the collecting container 128 which are consumables detachably mountable to the apparatus main assembly in the state that the door member is open are usable. The small door 8 as a portion-to-be-operated which is operated for mounting and demounting the consumables in the state that the door member is open is usable. The sheet feeding portion (such as the sheet feeding path and the feeding member) for feeding the sheet in the state that the door member is open is usable. The portion-to-be-operated (such as a lever or knob for moving the sheet feeding path or moving (rotating) the feeding member) for removing the sheet from the sheet feeding portion is usable. Further, at an inside portion of the collecting container door 10 as the door member, the operation guidance regarding the operation of the collecting container 128 may also be displayed.

Further, the present invention is also applicable to the case where the operation guidance regarding the object-to-be-operated disposed in the apparatus main assembly so as to oppose the door member, provided at a side surface other than the front side surface of the image forming apparatus, in the state that the door member is closed is projected onto the door member.

In the above-described embodiments, the present invention was applied to the color image forming apparatus, including the plurality of the image forming portions, but is also applicable to an image forming apparatus for a single color (for example, black), in which a single image forming portion is provided, so that it is possible to obtain effects similar to those in the above-described embodiments.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-236265 filed on Dec. 5, 2016, which is hereby incorporated by reference herein in its entirety.

What is claimed is:

1. An image forming apparatus comprising:
   a main assembly including an image forming portion configured to form an image on a sheet;
   a front cover mounted on a front side of said main assembly and configured to expose said image forming portion by being rotated from above toward below about a rotational axis crossing a vertical direction;
   a fixing portion configured to fix a position of said front cover in an open state;

an exchange unit detachably mountable to said image forming portion in the open state of said front cover;

an operating portion provided on the front side of said main assembly and configured to operate said image forming apparatus; and a projecting portion provided above said front cover with respect to the vertical direction and configured to project information regarding exchange of said exchange unit onto an inner surface of said front cover in the open state when said exchange unit is to be exchanged.

2. An image forming apparatus according to claim 1, wherein said front cover opens and closes by rotation about the rotational axis substantially parallel to a horizontal direction.

3. An image forming apparatus according to claim 1, wherein an angle formed between a surface on which the information regarding the exchange of said exchange unit is projected and a projection optical axis of said projecting portion is 90° or more and 135° or less.

4. An image forming apparatus according to claim 1, wherein said exchange unit is a developer container configured to supply a developer to said image forming portion.

5. An image forming apparatus according to claim 1, wherein said exchange unit is an image forming unit including an image bearing member.

6. An image forming apparatus according to claim 1, wherein said exchange unit is an accommodating container configured to accommodate a developer discharged from said image forming portion.

7. An image forming apparatus according to claim 1, further comprising an exchange unit detecting portion configured to detect mounting of said exchange unit, wherein said projecting portion switches information to be displayed on said front cover after a signal for detecting demounting of said exchange unit is outputted from said exchange unit detecting portion.

8. An image forming apparatus according to claim 1, wherein the information regarding the exchange of said exchange unit is character information.

9. An image forming apparatus according to claim 1, further comprising a front cover detecting portion configured to detect opening and closing of said front cover, wherein when the closing of the front cover is detected by said front cover detecting portion, said projecting portion stops projection.

10. An image forming apparatus according to claim 1, further comprising a displaying portion configured to display the information and a front cover detecting portion configured to detect opening and closing of said front cover, wherein said projecting portion starts projection after the information regarding the exchange of said exchange unit is displayed on said displaying portion and the opening of said front cover is detected by said front cover detecting portion.

* * * * *